(12) United States Patent
Becher et al.

(10) Patent No.: US 6,264,978 B1
(45) Date of Patent: *Jul. 24, 2001

(54) TRANSDERMAL APPLICATION SYSTEM CONTAINING ACETYLSALICYLIC ACID FOR ANTITHROMBOTIC THERAPY AND CANCER PROPHYLAXIS

(75) Inventors: Frank Becher, Koblenz; Thomas Kissel, Staufen, both of (DE)

(73) Assignee: LTS Lohmann Therapie-Systeme GmbH & Co. KG, Neuwied (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/256,065

(22) PCT Filed: Dec. 16, 1992

(86) PCT No.: PCT/EP92/02914

§ 371 Date: Aug. 4, 1994

§ 102(e) Date: Aug. 4, 1994

(87) PCT Pub. No.: WO93/12799

PCT Pub. Date: Jul. 8, 1993

(30) Foreign Application Priority Data

Dec. 20, 1991 (DE) .................................. 41 42 483

(51) Int. Cl.[7] .............................. A61F 13/00; A61F 13/02
(52) U.S. Cl. ........................... 424/449; 424/449; 424/448
(58) Field of Search .................................. 424/449, 448

(56) References Cited

U.S. PATENT DOCUMENTS

| | | | |
|---|---|---|---|
| 3,598,122 | 8/1971 | Zaffaroni | 424/435 |
| 4,012,508 | 3/1977 | Burton | 514/164 |
| 4,219,548 | 8/1980 | Reller | 514/786 |
| 4,460,368 | 7/1984 | Allison et al. | 424/449 |
| 4,640,689 | 2/1987 | Sibalis | 604/20 |
| 4,665,063 | 5/1987 | Bar-Shalom | 514/164 |
| 4,810,699 | 3/1989 | Sabatucci et al. | 514/161 |
| 4,975,269 | 12/1990 | Chavkin et al. | 424/45 |

FOREIGN PATENT DOCUMENTS

| | | |
|---|---|---|
| 0 055 635 | 7/1982 | (EP) . |
| 0 162 239 | 11/1985 | (EP) . |
| 1 757 | 4/1963 | (FR) . |
| 2 297 612 | 8/1976 | (FR) . |
| 2 144 326 | 3/1985 | (GB) . |
| 61-167 615 | 7/1986 | (JP) . |
| 1-203 336 | 8/1989 | (JP) . |
| 1-242521 | 9/1989 | (JP) . |
| 92 20343 | 11/1992 | (WO) . |

OTHER PUBLICATIONS

*New England Journ. of Medicine* 321, 183–185 (1989) Fuster et al "Aspirin in the Prevention of Coronary Disease".
*New England Journ. of Medicine* 325, 1593–1596, Thun et al "Aspirin Use and Reduced Risk of Fatal Colon Cancer" (1991).
Levy, "Clinical Pharmacokinetics of Aspirin", *Pediatrics 62,* 867–872 (1978).
Horsch "Die Salicylate", *Pharmazie* 34, 585–604 (1979).
Rowland et al "Kentics of Acetylsalicylic Acid Disposition in Man", *Nature* 215, 413–414 (1967).
Zichner et al "Zur optimalen Dosierung . . . " *Medizinische Klinik,* 85, 43–51 (1989).
Buchanan et al "Aspirin inhibits platelet function . . . " *Thrombosis Research* 25, 363–373 (1982).

*Primary Examiner*—Thurman K. Page
*Assistant Examiner*—Isis Ghali
(74) *Attorney, Agent, or Firm*—Collard & Roe, P.C.

(57) ABSTRACT

The invention concerns a transdermal application system for antithrombotic therapy and for the prophylaxis against cancer, respectively, containing as active substance acetylsalicylic acid and/or pharmaceutically acceptable salts thereof.

8 Claims, No Drawings

TRANSDERMAL APPLICATION SYSTEM CONTAINING ACETYLSALICYLIC ACID FOR ANTITHROMBOTIC THERAPY AND CANCER PROPHYLAXIS

The platelet aggregation-preventing effect of acetylsalicylic acid (ASA) and its effect in the prevention of cardiac thrombosis was described in the late 60s. Subsequently, a large number of clinical studies have been conducted whereby ASA was administered orally in the case of the following indications:

prevention of first-instance cardiac infarction, prevention of reinfarction, treatment of unstable angina pectoris, prophylaxis against thrombosis after transplantation of vascular prostheses or artificial cardiac valves prophylaxis against thrombosis of the peripheral arterial vessels prophylaxis against thrombosis of inadequate cerebral circulation Where in the following the term "anti-thrombotic therapy" is used, this substantially comprises the above indications.

In recent years, the results of these therapeutic tests on patients have been summed up (V. Fuster et al., "Aspirin in the prevention of coronary disease", New Engl. J. Med. 321, 183–185 (1989) and R. Zichner et al., "Zur optimalen Dosierung von Acetylsalicylsaeure", Med. Klin. 84, 43–51 (1989)).

Acetylsalicylic acid has frequently been employed in medical practice as a non-steroid anti-inflammatory, analgesic and antipyretic active substance. ASA influences platelet function and prevents thrombosis by irreversibly inhibiting the thromboxane A2 synthesis (M. Buchanan et al., "Aspirin inhibits platelet function independent of cyclooxygenase", Thrombosis Res. 25, 363–373 (1982)).

After oral administration ASA is quickly absorbed. However, its biological half-life in the systemic circulation is very short, it lasts only 15–20 minutes (M. Rowland et al., "Kinetics of acetylsalicylic acid disposition in man", Nature 215, 413–414 (1967)). In normal adults ASA is quickly hydrolyzed to salicylic acid in the gastrointestinal tract. (G. Levy, "Clinical pharmacokinetics of aspirin", Pediatrics 62, 867–872 (1978)).

It should be emphasized, however, that it is ASA itself which is active in inhibiting platelet function, and not its hydrolysis product, salicylic acid (W. Horsch, "Die Salicylate", Pharmazie 34, 585–604 (1979)).

Acetylsalicylic acid (ASA) is continually taken by large parts of the population especially in the USA. According to a paper by Thun et al., "Aspirin Use and Reduced Risk of Fatal Colon Cancer", New Engl. J. Med. 325, 1593–1596 (1991), ASA reduces mortality caused by colonic cancer by around 50%, provided ASA is taken continually, i.e. on at least 16 days per month. The study involved more than 660,000 persons living in all 50 states of the USA, the District of Columbia and Puerto Rico, who had taken ASA for a period of at least one year. This study refers only to the use of ASA and fails to provide further information as to the manner and form of administration and dosage. Nevertheless, it is to be assumed that ASA was administered orally and that the substance having the above-described effect was not the hydrolysis product salicylic acid but ASA itself.

In antithrombotic therapy oral administration is practised almost exclusively; in the case of anti-inflammatory, analgesic and antipyretic indications, however, attempts have already become known to apply the active substance via the skin. Thus, U.S. Pat. No. 3,598,122 mentions ASA as a possible antipyretic active substance in a membrane-controlled transdermal therapeutic system. FR-M 1757 describes the dermal topical application of an oil-in-water emulsion containing 5% of ASA against acute pain. FR-A 2 297 612 claims liniments and ointments containing ASA as analgetic agent. In U.S. Pat. No. 4,012,508 ASA is employed in combination with corticosteroids for topical application in the case of dermatological indications. U.S. Pat. No. 4,219,548 describes a topical application of ASA for the checking of inflammatory processes. In EP-A 0 055 635 an ASA-containing gel is applied topically in the case of anti-inflammatory, analgesic and antipyretic indications. U.S. Pat. No. 4,460,368 discloses a device for the transdermal application of ASA out of an aqueous system for achieving antiinflammatory and analgesic effects. In U.S. Pat. No. 4,665,063, ASA is topically applied against dermatological disturbances by using a solution in ethanol. In U.S. Pat. No. 4,640,689 an increase in the penetration rate of ASA in transdermal application is achieved by employing electric current.

Addition of suitable penetration enhancers, as in EP-A 0 162 239, also leads to an improved penetration of ASA through the skin. In Japanese Publication 61 167 615 ASA is applied to the skin by means of a film. U.S. Pat. No. 4,810,699 describes combinations of ASA with other active substances for the transdermal treatment of inflammations, pain and fever. Japanese Patent 1,203,336 relates to special penetration enhancers for the transdermal application of ASA as an analgesic. Further substances of this kind for ASA in transdermal application for the checking of inflammatory processes, are contained in Japanese Patent 1,242,521. Finally, U.S. Pat. No. 4,975,269 relates to storage-stable solutions of ASA for topical application aiming at checking inflammatory processes and relieving pain.

The mentioned prior art does not contain any indication, nor can it be derived therefrom, that the use of a transdermal system has been considered which contains ASA and/or pharmaceutically acceptable salts thereof to prevent platelet aggregation in humans and/or for the prophylaxis against cancer.

Many formulations and compositions contain water or hydrophilic solvents which accelerate the hydrolysis of ASA to salicylic acid. Since, as explained hereinabove, salicylic acid has no antithrombotic effect but shows an anti-inflammatory and analgesic effect comparable to that of ASA, it becomes clear that the decomposition of ASA in the above mentioned application systems has not been studied in detail.

It has therefore been the object of the present invention to provide an application system for the application of ASA and/or its pharmaceutically acceptable salts for antithrombotic therapy and/or for the prophylaxis against cancer which avoids the disadvantages inherent in oral application and allows for target-specific dosage of the unchanged active substance.

This object has surprisingly been solved by employing a transdermal system for administering acetylsalicylic acid and/or the pharmaceutically acceptable salts thereof for antithrombotic therapy and/or for the prophylaxis against cancer, said system preferably containing acetylsalicylic acid or the said salts in a matrix substantially suppressing or preventing the hydrolysis of acetylsalicylic acid. In other words, the system preferably is free of substances which—under storage conditions or during application—lead to a separation of the acetyl group.

A transdermal administration system offers the following advantages in antithrombotic therapy:
1. ASA is directly introduced into the systemic circulation in its pharmacologically active form, thus avoiding metabolism in the gastrointestinal tract.
2. reduction of gastrointestinal side effects
3. constant therapeutic effect with reduced doses of ASA
4. reduced risk of overdosage
5. treatment of outpatients without the need of observation
6. improved patient compliance during treatment.

The content of ASA in such an administration unit is generally 5–500 mg, preferably 30–200 mg, or the corresponding amount of a pharmaceutically acceptable salt. ASA salts suitable for this purpose are all those which are non-toxic and pharmacologically effective, such as lithium, sodium, potassium, magnesium and calcium salts or salts of ASA with basic organic compounds, such as lysine, arginine or cetrimide (hexadecyltrimethylammonium bromide). The speed and extent of the transdermal permeation of ASA into the body is, naturally, dependent on the given amount, the type of compound (free acid or salt) and possibly also on the presence of auxiliary substances, such as penetration enhancers. Advantageously, the system is adjusted such that an ASA blood level of between 0.1 and 1.0 µg/ml is obtained. For practical application, the content is advantageously adjusted to the type of matrix, the recommended period of time during which the plaster is worn, the intended indication, the body weight (child or adult), the permeability of the matrix or membrane of the plaster, and the permeation through the skin.

In antithrombotic therapy and in the prophylaxis against cancer, a therapeutically effective amount of ASA and/or ASA salts in the blood corresponds to blood level values of ASA of between 0.1 and 1.0 µg/ml. Although, after oral administration, ASA is quickly absorbed, this mode of administration is disadvantageous due to the hydrolysis of ASA to salicylic acid, especially when taking into account the short biological half-life and the fact that for prophylaxis an administration is aimed at which remains as constant as possible. By contrast, the transdermal treatment as proposed in the present invention secures rather constant and reproducible blood levels of ASA which are especially effective in antithrombotic therapy and suitable for cancer prophylaxis. A delivery system according to the invention, however, ensures constant and reproducible ASA blood levels which are effective in antithrombotic therapy.

The term cancer prophylaxis implies, for example, the prophylaxis against cancer involving formation of tumors, for example, in the gastrointestinal tract, such as colonic cancer.

The transdermal application system for ASA and/or ASA salts according to the present invention, may be realised in numerous ways, for example in the form of a plaster, in particular a pressure-sensitive adhesive one, a film, a spray, a cream, ointment and the like. The preferred form of administration is that of a pressure-sensitive adhesive plaster comprising an impermeable backing layer, an active substance reservoir connected thereto and consisting of a polymer matrix, where other control mechanisms are not present a membrane controlling the release of active substance, a pressure-sensitive adhesive device for fixing the system to the skin and, if required, a protective layer which may be detached prior to the application of the system. With all forms of administration, the matrix forming the reservoir must be chosen such that hydrolysis of ASA is precluded or is at least greatly reduced. A hydrophobic adjustment of the matrix is more suitable for this purpose than a hydrophilic one.

For reducing or suppressing the hydrolysis, substances may be added such as acylating agents, preferably acetylating agents, and, in particular, acetic anhydride, for instance in an amount of 0.01 to 3, preferably 0.1 to 2% wt, relative to acetylsalicylic acid.

The transdermal pressure-sensitive adhesive plasters suitable for this invention are all known to those skilled in the art from the prior art. For the most part, these plasters can be assigned to two basic control principles: matrix diffusion control and membrane control, whereby only the latter allows for an active substance release of zero order. A matrix diffusion control plaster is described, for example, in German Patent No. 33 15 272. It consists of an impermeable backing layer, a reservoir made up of a polymer matrix connected thereto and containing the active substance in a concentration which is above the saturation concentration, a pressure-sensitive adhesive layer connected to the reservoir and permeable to the active substance, and a protective layer which covers the pressure-sensitive adhesive layer, e.g. a siliconised film of polyester, in particular of polyethylene terephtalate, and may be detached for application of the system. If the reservoir matrix itself is pressure-sensitive adhesive, the additional pressure-sensitive adhesive layer need not be present. However, systems with a saturation below the saturation concentration are possible as well. Examples for plasters with membrane control include U.S. Pat. No. 3,742,951, 3,797,494, 3,996,934 and 4,031,894. These plasters, in principle, consist of a backing layer (e.g. a film of polyester, such as polyethylene terephtalate, which may be aluminized, or an aluminized film of a synthetic resin, such as polypropylene, nylon, polycaprolactam), which forms one of the surfaces, a membrane, an adhesive layer permeable to the active substance which forms the other surface and, finally, a reservoir containing the active substance between the two layers forming the surfaces. Alternatively, the active substance may also be contained in a plurality of microcapsules dispersed within the permeable adhesive layer. In all cases, the active substance is continuously released from the reservoir or the microcapsules, through a membrane, into the adhesive layer which is permeable to the active substance and which is in contact with the skin of the person to be treated. If microcapsules are present, the capsule material may also serve as a membrane. Substances suitable for membranes and microcapsules are described, for example, in U.S. Pat. No. 3,996,934.

In addition, it should be pointed out that control is also possible by means of electric current, whereby the velocity is determined by the phase in which the active substance permeates the skin. Such processes are referred to as electroosmosis, iontophoresis or electrophoresis.

All types of plasters may, if required, contain various additives in addition to the matrix forming the reservoir and the active substance, the latter also including combinations of ASA and the salts thereof, in order to achieve the desired properties. To be mentioned in particular are those additives enhancing the permeation of ASA and/or its pharmaceutically acceptable salts through the skin. The various suitable additives are known to those skilled in the art, a detailed list is therefore unnecessary; however, glycerin, 1,2-propane diol, the monomethyl or monoethyl ether, respectively, of ethylene glycol, 2-octyl dodecanol, the laurate, palmitate, stearate or oleate of sorbite, $C_8$–$C_{10}$-ethoxylated oleic acid glycerides, lower alkyl($C_1$ to $C_3$) esters of lauric acid, such as propylene glycol mono-laurate, lauric, capric, oleic acid, etc., are mentioned by way of example. The amount used is generally 0 to 20% wt., preferably 0.5 to 10% wt., relative to the total matrix components. Said amount is dependent on the type of matrix, the permeability of the matrix or membrane, respectively, of the plaster, the dissolving capacity of the penetration enhancer for the active substance, and the permeation through the skin.

The present invention will be illustrated but not limited by the following examples:

EXAMPLES

1. Acrylate-based Single-Layer System 5 g dioctyl cyclohexane, 8 g acetylsalicylic acid and 40 mg acetic anhydride are added to 100 g of a solution of an acrylic adhesive (e.g. Durotak® 280–2516 National Starch and Chemical) having a solids content of 42% wt., and the solution is homogenized by agitating.

The solution is thereafter spread at a thickness of 300 μm on a 100 μm thick siliconized polyester film. In the finished system, this film takes over the function of the detachable protective layer and must be removed prior to use. The moist film is dried for 20 minutes at 50° C. and thereafter has a weight per area of 100 g/m².

The dried film is subsequently laminated with a 12 μm thick polyester film and the finished plasters are punched out of the laminate.

2. Multilayer System

The finished system comprises a detachable protective layer, a spread of skin adhesive, a non-adhesive reservoir, a backing layer impermeable to active substance and a basic spread, having good viscous properties, which is located between the reservoir layer and the backing layer and performs the function of fixing the non-adhesive reservoir to the backing layer.

A. Manufacture of the Skin Adhesive Spread 100 g of a block polymer consisting of polystyrene and polyisoprene (e.g. Cariflex® TR-1107, Fa. Shell), 175 g of a glycerol ester of partially hydrogenated colophonium and 50 g of dioctyl cyclohexane are dissolved in 500 g n-heptane and, subsequently, 15 g acetylsalicylic acid and 150 mg acetic anhydride are added thereto. The mass is homogenized by agitating and then spread on a siliconized polyester film at a thickness of 100 μm, the polyester film serving in the finished product as a detachable protective layer. The moist film is dried for 20 minutes at 50° C. and thereafter has a weight per area of 25 g/m².

B. Manufacture of the Reservoir Spread 100 g of a block polymer consisting of polystyrene and polyisoprene (e.g. Cariflex TR-1107, Fa. Shell)

and 20 g dioctyl cyclohexane are dissolved in 120 g n-heptane.

Thereafter, 40 g acetylsalicylic acid and 40 mg acetic anhydride are added, and the mass is homogenized by agitating. The resulting mass is spread at a thickness of 300 μm on a protective polyester film which is siliconized to a higher degree than the detachable protective layer, and is dried for 20 minutes at 50° C. The dried reservoir layer has a weight per area of 100 g/m²

C. Manufacture of the Basic Spread 100 g of a block polymer consisting of polystyrene and polyisoprene (e.g. Cariflex TR-1107, Fa. Shell), 175 g of a glycerol ester of partially hydrogenated colophonium and 50 g of dioctyl cyclohexane are dissolved in 500 g n-heptane and, analogous to B, spread, at a thickness of 100 μm, onto a polyester film which has been siliconized to a higher degree than the detachable protective layer, and is dried for 20 minutes at 50° C. The dried film has a weight per area of 25 g/m²

D. Assembly of the Entire System and Punching of the Individual Plasters

The reservoir spread resulting from B is laminated onto the skin adhesive spread A; the foil mentioned under B which is siliconized to a higher degree is thereafter removed. Then the basic spread C is applied in the same manner and after removal of the film mentioned under C which has a higher degree of siliconization, a 12 μm thick polyester film is laminated thereon.

The finished plasters are punched out of the assembled laminate.

3. Membrane System

A heat-sealing laminate consisting of a flexible polyester film and a film of a polyethylene/vinylacetate copolymer is sealed against a 50 μm thick membrane of a polyethylene/vinylacetate copolymer, having a vinyl acetate content of 19%, in the dimensions and shapes corresponding to those of the intended plasters and in such a manner that a kind of flat bag is obtained. The sealing seam is to be 4 mm in width. Before the bag is sealed in such a manner that no gaps remain, it is filled with a liquid preparation of silicon oil with 10% acetylsalicylic acid and 0.05% acetic anhydride.

The membrane side of the bag is then laminated on a silicone-based skin adhesive spread, which is located on a suitable foil having been rendered adhesive. This foil is identical with the detachable protective layer.

The finished systems are punched out in such a manner that a bag having a sealing border of 3 mm in width remains.

What is claimed is:

1. A transdermal therapeutic application system useful for antithrombotic therapy, for applying through the skin of a person, an effective antithrombotic amount of an active ingredient consisting essentially of acetyl salicylic acid or a non-toxic pharmaceutically acceptable salt thereof or a combination thereof;

said transdermal therapeutic application system consisting essentially of a matrix having a substance such that hydrolysis of acetyl salicylic acid is precluded or is at least greatly reduced; and said matrix containing a substance being selected from the group consisting of dioctyl cyclohexane, dioctyl cyclohexane dissolved in n-heptane, glycerol ester of partially hydrogenated colophonium and dioctyl cyclohexane dissolved in n-heptane, and silicone oil.

2. The transdermal therapeutic application system of claim 1, wherein said matrix further contains acetic anhydride.

3. The transdermal therapeutic application system of claim 1, comprising an impermeable backing layer;

said matrix being an active substance reservoir connected thereto and made of polymer;

a membrane controlling the release of the active ingredient;

a pressure-sensitive adhesive device for fixing the system to the skin; and a protective layer which may be detached prior to the application of the system.

4. A therapeutic method for preventing thrombosis in a person, comprising administering through a transdermal therapeutic application system applied to the skin of said person, an effective antithrombotic amount of an active ingredient consisting essentially of acetyl salicylic acid or a non-toxic pharmaceutically acceptable salt thereof or a combination thereof; and said transdermal application system comprising a matrix containing a substance such that hydrolysis of acetyl salicylic acid is precluded or is at least greatly reduced.

5. The therapeutic method of claim 4 wherein said matrix further contains acetic anhydride.

6. The therapeutic method of claim 4, further comprising utilizing an electric current to enhance the permeation of the active ingredient through the skin.

7. The therapeutic method of claim 4, wherein said effective amount comprises between 5 and 500 mg.

8. The therapeutic method of claim 7, wherein said effective amount comprises between 30 and 200 mg.

\* \* \* \* \*